United States Patent
Glasmachers et al.

(10) Patent No.: US 10,488,451 B2
(45) Date of Patent: Nov. 26, 2019

(54) METHOD FOR OPERATING AN INDUCTIVE CONDUCTIVITY MEASURING DEVICE AND RESPECTIVE INDUCTIVE CONDUCTIVITY MEASURING DEVICE

(71) Applicant: KROHNE Messtechnik GmbH, Duisburg (DE)

(72) Inventors: Holger Glasmachers, Bochum (DE); Philipp Mertmann, Bochum (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 144 days.

(21) Appl. No.: 15/821,958

(22) Filed: Nov. 24, 2017

(65) Prior Publication Data
US 2018/0149684 A1   May 31, 2018

(30) Foreign Application Priority Data
Nov. 25, 2016   (DE) ........................ 10 2016 122 800

(51) Int. Cl.
*G01R 31/00* (2006.01)
*G01R 27/26* (2006.01)

(52) U.S. Cl.
CPC ................................ *G01R 27/2611* (2013.01)

(58) Field of Classification Search
USPC ....................................... 324/654, 700, 71.1
See application file for complete search history.

(56) References Cited

U.S. PATENT DOCUMENTS

| | | | |
|---|---|---|---|
| 4,604,581 A * | 8/1986 | Thadani ................... | G01V 3/28 324/339 |
| 5,003,267 A | 3/1991 | Coleman | |
| 8,847,608 B2 * | 9/2014 | Rapoport ............. | G01N 24/085 324/309 |
| 2009/0267617 A1 | 10/2009 | Seyfi et al. | |
| 2012/0126798 A1 * | 5/2012 | Rondinone .......... | G01N 17/006 324/229 |
| 2013/0038337 A1 * | 2/2013 | Rodfalk ................. | B22D 2/003 324/633 |
| 2017/0261588 A1 | 9/2017 | Andelic | |

OTHER PUBLICATIONS

A.M. Bunyak, I.I. Tsapiv and V.P. Koval'Chuk; Resonant LC Circuit as a Contactless Conductometric Converter; Plenum Publishing Corporation, New York, NY; 1975; pp. 1764-1767.

* cited by examiner

*Primary Examiner* — Vincent Q Nguyen

(74) *Attorney, Agent, or Firm* — David S. Safran; Roberts Mlotkowski Safran Cole & Calderon, P.C.

(57) ABSTRACT

A method for operating an inductive conductivity measuring device that has a transmitting coil with an input and a receiving coil, the transmitting coil and the receiving coil being inductively coupled to one another by an electrically conductive medium. An electrical preset alternating signal is generated and fed to the input of the transmitting coil. The method for operating an inductive conductivity measuring device is improved in that a frequency of a preset alternating signal is varied in a frequency interval, in the frequency interval, a frequency-dependent minimum input impedance at the input of the transmitting coil is determined using a response alternating signal, a minimum frequency of the response alternating signal is determined at the minimum input impedance at the input of the transmitting coil, and a conductivity of the medium is determined using the minimum frequency of the response alternating signal.

5 Claims, 3 Drawing Sheets

METHOD FOR OPERATING AN INDUCTIVE CONDUCTIVITY MEASURING DEVICE AND RESPECTIVE INDUCTIVE CONDUCTIVITY MEASURING DEVICE

BACKGROUND OF THE INVENTION

Field of the Invention

The invention relates, on the one hand, to a method for operating an inductive conductivity measuring device. The conductivity measuring device has a transmitting coil and a receiving coil for carrying out the method and the transmitting coil, in turn, has an input. The transmitting coil and the receiving coil are inductively coupled to one another by an electrically conductive medium. In the method, an electrical preset alternating signal is generated and supplied to the input of the transmitting coil.

The invention relates, on the other hand, to an inductive conductivity measuring device. The conductivity measuring device likewise has a transmitting coil, a receiving coil, and a control unit for, among other things, controlling the transmitting coil and the receiving coil. In turn, the transmitting coil has an electrical input. The control unit is thereby designed to generate an electrical preset alternating signal and to supply the preset alternating signal to the input of the transmitting coil. During operation of the inductive conductivity measuring device, the transmitting coil and the receiving coil are inductively coupled to one another by an electrically conductive medium.

Description of Related Art

Inductive conductivity measuring devices can also be used in aggressive and corrosive media such as industrial waste water, seawater and acidic solutions. This is possible because, in contrast to the electrodes of a conductive conductivity measuring device, both the transmitting coil and the receiving coil do not have to be in direct contact with a medium, but may be surrounded by a housing that is resistant to aggressive and corrosive media without the functionality being impaired. Since there is no direct contact with aggressive and corrosive media in the presence of a housing, inductive conductivity sensors are characterized by a long service life and by a substantial maintenance freedom compared to conductive conductivity measuring devices. The housings also make them suitable for hygienic applications in processes in the branches of food, beverage and pharmaceuticals.

An electrical input of an electrical coil, such as the transmitting coil or the receiving coil, usually has two electrical terminals, via which an electrical signal, such as the electrical preset alternating signal, is fed to the coil. The inductive coupling of the transmitting coil and the receiving coil with one another via the electrically conductive medium is effected in that the preset alternating signal fed to the transmitting coil generates eddy currents in the medium and the eddy currents induce a receive alternating signal, for example in the form of a voltage, in the receiving coil. Thus, a preset alternating signal causes a receive alternating signal.

It is known from the prior art to determine an electrical conductivity of a medium from the ratio of an amplitude of a receive alternating signal and an amplitude of a preset alternating signal. Analog electronic circuits, such as e.g., analog lock-in amplifiers, are used to determine an amplitude of an alternating signal. However, a problem in the determination of amplitudes using analog electronic circuits is that the accuracy of the determination of an amplitude, and thus, also the accuracy of the determination of a conductivity of a medium depends on the accuracy of the electronic circuit. The accuracy of an analog electronic circuit is impaired by drifts and tolerances of the components of the electronic circuit.

SUMMARY OF THE INVENTION

Thus, the object of the invention is to provide a method for operating an inductive conductivity measuring device and to provide an inductive conductivity measuring device, in which the accuracy of a determination of a conductivity of a medium is improved compared to the prior art.

According to a first teaching, the invention relates to a method for operating an inductive conductivity measuring device, in which the above object is achieved. The method according to the invention is initially characterized essentially by the following method steps:

In a first method step, a frequency of the preset alternating signal is varied in a frequency interval. The variation of the frequency, thus, is effected within the frequency interval.

In a second method step, a frequency-dependent minimum input impedance at the input of the transmitting coil is determined, in this frequency interval, using a response alternating signal. In this case, the response alternating signal is caused by the preset alternating signal by means of the transmitting coil. When, e.g., the preset alternating signal causes a voltage across the input of the transmitting coil and the voltage, thus, represents a transmit alternating signal, then the response alternating signal is a current caused by the voltage through the transmitting coil and vice versa. The input impedance is the quotient of the voltage and the current. This method step is based on the recognition that the input impedance at the input of the transmitting coil is a frequency-dependent variable having a real part and an imaginary part. The real part is also referred to as the resistance and the imaginary part as the reactance. The magnitude and phase of the input impedance are determined from the resistance and the reactance and are dependent on the frequency of the preset alternating signal, wherein the frequency of the preset alternating signal and the frequency of the response alternating signal are identical. The minimum input impedance is thereby usually the input impedance with the smallest magnitude of input impedance within the frequency interval. In most cases, the first and the second method step are carried out together.

In a third method step, a minimum frequency of the response alternating signal is determined at the minimum input impedance at the input of the transmitting coil. The minimum frequency is, thereby, precisely the frequency of the response alternating signal and thus also of the preset alternating signal, in which the input impedance is minimal.

In a fourth method step, a conductivity of the medium is determined using the minimum frequency of the response alternating signal. This method step is based on the recognition that the minimum frequency is a function of the conductivity of the medium. The function is determined, for example, by carrying out the method with different media, wherein each of the different media has a different known conductivity. It has been found that the sensitivity, i.e., a change in the minimum frequency with respect to a change in the conductivity, decreases outside a conductivity measuring range that has a dynamic range of conductivity of about 100. In this manner, the minimum frequency changes e.g., in a conductivity range of 20 mS/cm to 2 S/cm (2 S/cm divided by 20 mS/cm equals 100) by a factor of 2. The sensitivity decreases outside of this conductivity range.

The method according to the invention has the advantage over the method known from the prior art that the determination of the conductivity of the medium is more accurate. The higher accuracy is a result of a frequency of an alternating signal being determined instead of amplitudes of variables. It has been shown that with the same technical effort and, thus, the same costs, the determination of a frequency can be implemented more accurately than the determination of an amplitude.

In one implementation of the method according to the invention for operating an inductive conductivity measuring device, in which the transmitting coil, the receiving coil and the medium form an electrical resonant circuit having a resonant frequency, it is provided that in determining the minimum input impedance and the minimum frequency, the resonant frequency of the resonant circuit is determined. This implementation is based on the recognition that the transmitting coil, the receiving coil and the medium together form a resonant circuit with a resonant frequency. In this case, the transmitting coil, the receiving coil and the medium have the necessary inductive and capacitive components for a resonant circuit. Furthermore, it has been recognized that there is a correlation between the inductive components that determine the resonant frequency and the conductivity of the medium.

Thus, the conductivity can be determined from the resonant frequency and also from the input impedance. While the inductive components of the transmitting coil and the receiving coil are essentially desired characteristics, the capacitive components are essentially undesirable characteristics of the transmitting coil and the receiving coil. It is known from the prior art to minimize capacitive properties, i.e., parasitic capacitances, of coils, which is contrary to the method according to the invention. In addition to parasitic capacitances e.g., capacitors are also provided for the implementation of the resonant circuit and/or for setting the resonant frequency of the resonant circuit. The resonant frequency is the frequency of the resonant circuit at which the reactance of the input impedance is zero and, thus, the input impedance has only a resistance. Consequently, the magnitude of the input impedance at the resonance frequency is also minimum, which is why the resonance frequency corresponds to the minimum frequency.

In a further implementation of the method for operating an inductive conductivity measuring device, which has a measuring resistor at the input of the transmitting coil, it is provided that a measuring voltage is measured across the measuring resistor as the response alternating signal. Alternatively, a measuring current through the measuring resistor can be determined as the response alternating signal. The measuring current is e.g., determined from the measuring voltage and a resistance value of the measuring resistor. The measuring resistor is preferably electrically connected in series with the input of the transmitting coil. This means that if there are no other components, the same current will flow through the transmitting coil and the measuring resistor. In combination with the above implementation, the resonant frequency of the resonant circuit is determined by determining a maximum amplitude of the measuring voltage across the measuring resistor in the frequency interval. At the maximum amplitude of the measuring voltage, the resonance frequency is present, which corresponds to the minimum frequency. To determine the amplitude of the measuring voltage, for example, an analog lock-in amplifier is used. When using an analog lock-in amplifier, absolute errors in the determination of the amplitude of the measuring voltage are insignificant since the maximum amplitude of the measuring voltage is determined in relation to the course of the amplitude of the measuring voltage over the frequency interval.

According to a second teaching, the invention relates to an inductive conductivity measuring device, in which the stated object is achieved. The inductive conductivity measuring device according to the invention is initially characterized essentially in that the control unit is designed, during operation of the inductive conductivity measuring device, to vary a frequency of the preset alternating signal in a frequency interval, to determine, in the frequency interval, a frequency-dependent minimum input impedance at the input of the transmitting coil using a response alternating signal, to determine a minimum frequency of the response alternating signal at the minimum input impedance at the input of the transmitting coil, and to determine a conductivity of the medium using the minimum frequency of the response alternating signal.

One design of the inductive conductivity measuring device provides that the control unit is designed for carrying out one of the described methods.

In one design of the inductive conductivity measuring device, it is provided that the receiving coil has an electrical input and the input is terminated with a terminating resistor. This means that the receiving coil and the terminating resistor are electrically connected in parallel. This design is based on the finding that the conductivity measuring range of the inductive conductivity measuring device, which has a high sensitivity, can be shifted by selecting a resistance value $R_A$ of the terminating resistor. The following formula can be used to calculate the resistance value of the terminating resistor:

$$\frac{U_E}{U_S} = \frac{N_E}{N_S} \frac{1}{1 + N_E^2 R_W \left( \frac{1}{R_A} + \frac{1}{j\omega L_E} \right)}$$

In this formula, $U_E$ is a receive alternating signal in the form of a voltage across the input of the receiving coil, $U_S$ is a transmit alternating signal in the form of a voltage across the input of the transmitting coil, $N_E$ is a number of turns of the receiving coil, $N_S$ is a number of turns of the transmitting coil, $R_W$ is a resistance value of the medium from which the conductivity of the medium is determined using the geometry of the medium, $L_E$ is an inductance of the receiving coil, $\omega$ is an angular frequency of the preset alternating signal and j an imaginary unit.

The explanations relating to the method according to the invention apply correspondingly to the inductive conductivity measuring device and vice versa.

In detail, a plurality of possibilities exists for designing and further developing the method according to the invention for operating an inductive conductivity measuring device and for the inductive conductivity measuring device as will be apparent from the following description of a preferred embodiment in conjunction with the accompanying drawings.

DETAILED DESCRIPTION OF THE INVENTION

Figure 1:
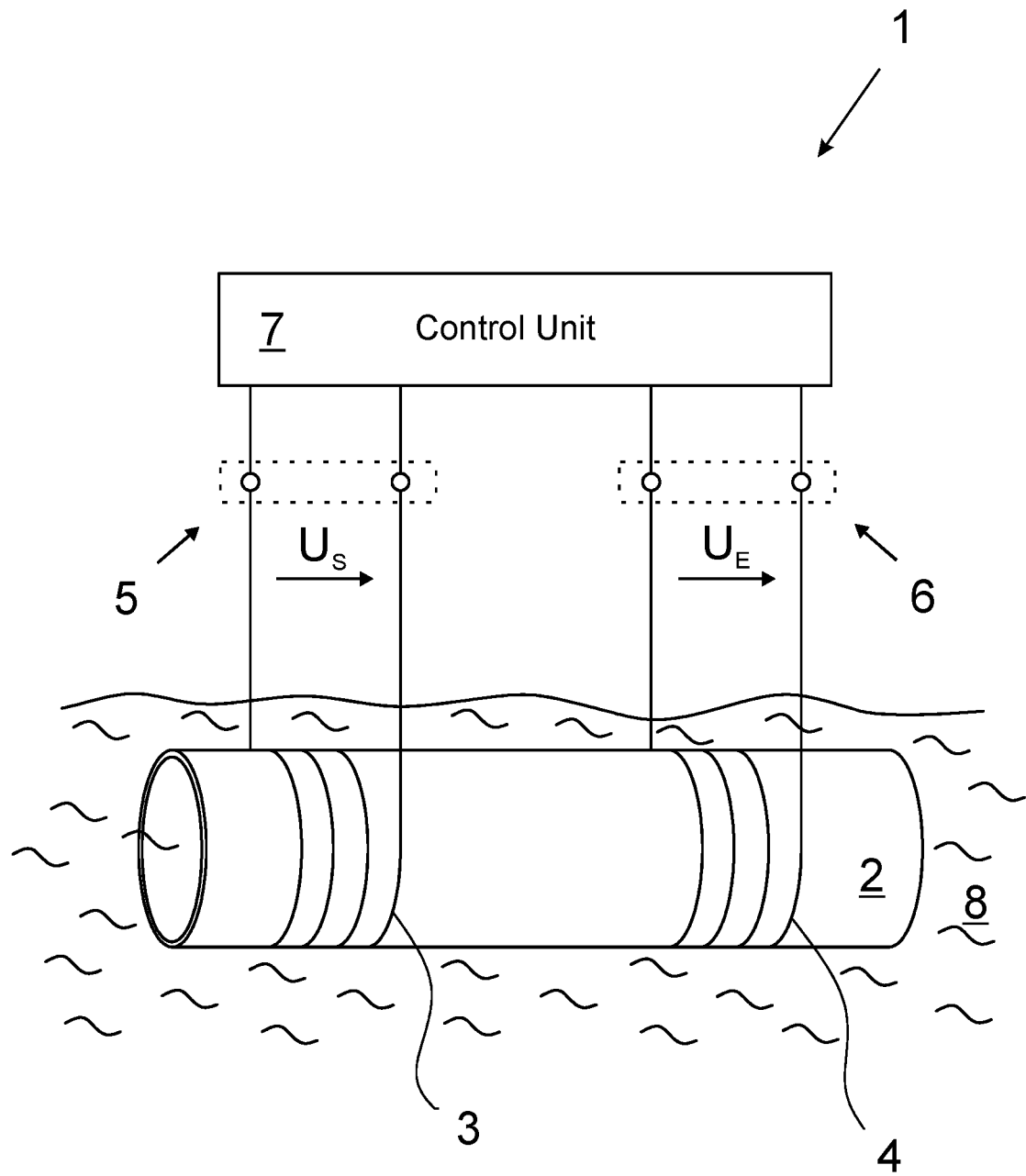
FIG. 1 schematically depicts an embodiment of an inductive conductivity measuring device.

FIG. 1 shows the inductive conductivity measuring device 1. The inductive conductivity measuring device 1 has the hollow-cylindrical carrier 2, on which the transmitting coil 3 and the receiving coil 4 are arranged. The transmitting coil 3 and the receiving coil 4 are arranged on the hollow cylindrical carrier 2 by being wound around the hollow cylindrical carrier 2, wherein the transmitting coil 3 has the number $N_S$ of turns and the receiving coil 4 has the number $N_E$ of turns. Furthermore, the transmitting coil 3 has the input 5 and the receiving coil 4 has the input 6. The inductive conductivity measuring device 1 also has the control unit 7. The control unit 7 is designed to control the transmitting coil 3 and the receiving coil 4, which is why the control unit 7 is also electrically connected to the input 5 of the transmitting coil 3, on the one hand, and to the input 6 of the receiving coil 4, on the other hand.

The hollow cylindrical carrier 2 having the transmitting coil 3 and the receiving coil 4 is immersed in the medium 8 and the inductive conductivity measuring device 1 is in operation. The medium 8 surrounds the hollow cylindrical carrier 2 and is also present in the inner space of the hollow cylindrical carrier 2. The medium 8 is electrically conductive and thereby couples the transmitting coil 3 and the receiving coil 4 inductively with one another. Since this is an abstracted schematic representation of the inductive conductivity measuring device 1, a housing that is usually present, which prevents direct contact of the transmitting coil 3 and the receiving coil 4 with the medium 8, is not shown here. By avoiding contact of the transmitting coil 3 and the receiving coil 4 with the medium 8, it is possible to use the inductive conductivity measuring device 1, in contrast to conductive conductivity measuring devices, in aggressive and corrosive media such as industrial waste water, seawater and acidic solutions without the functionality of the inductive conductivity measuring device 1 being limited. The housing also makes it suitable for hygienic applications in processes in the branches of food, beverage and pharmaceuticals.

Figure 2:
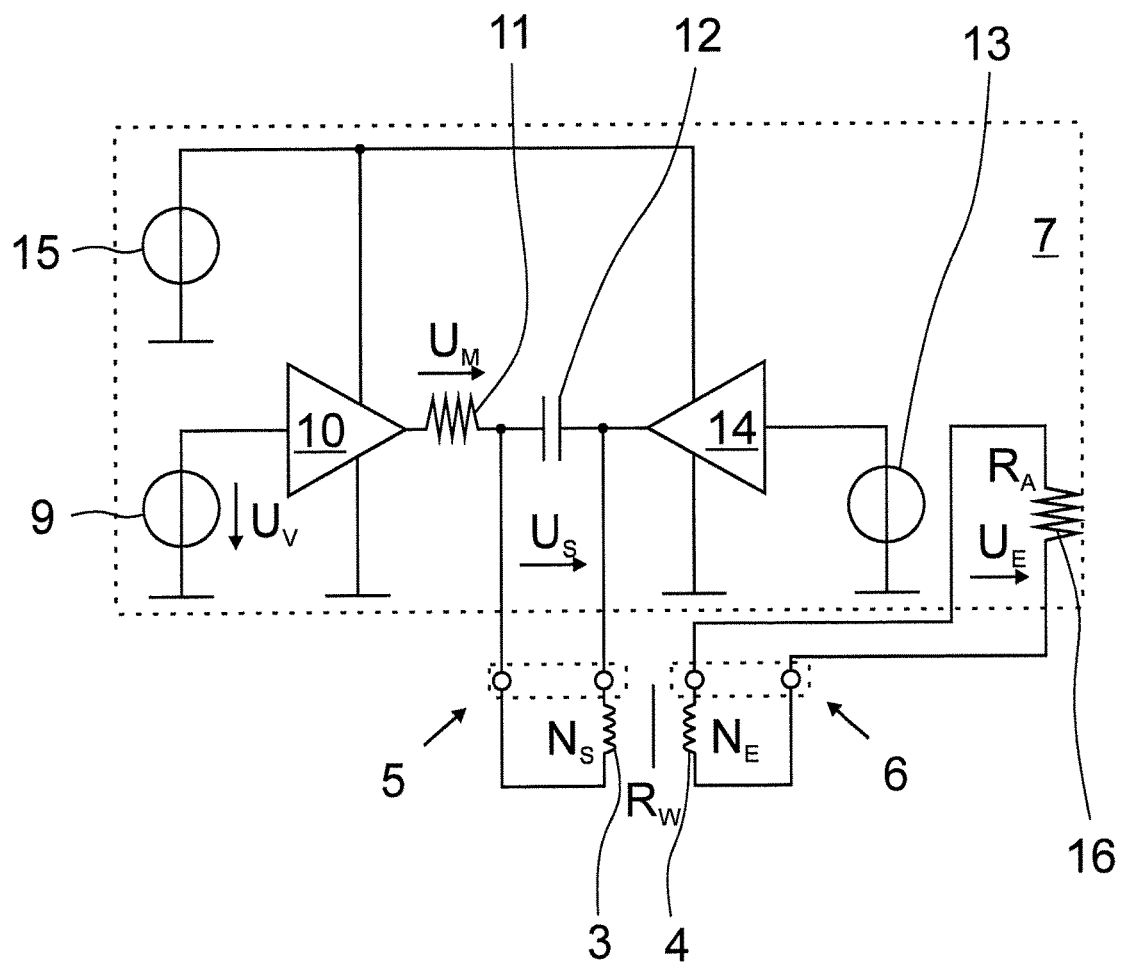
FIG. 2 is a representation of a part of the electrical circuit of the inductive conductivity measuring device of FIG. 1

FIG. 2 shows a representation of a part of the electrical circuit of the inductive conductivity measuring device 1. The control unit 7 is designed to generate the electrical preset alternating signal $U_V$ and to supply the preset alternating signal $U_V$ to the input 5 of the transmitting coil 3, wherein the transmit alternating signal $U_S$ is then applied at the input 5 of the transmitting coil 3. For this, the control unit 7 has the alternating signal source 9 and the first amplifier 10. The alternating signal source 9 generates a preset alternating signal $U_V=1.5V+1.4V \sin(\omega t)$, which is comprised of the constant voltage of 1.5V and the sinusoidal voltage of 1.4V modulated with the angular frequency $\omega$. The first amplifier 10 has a gain of 1 and thus serves as a buffer amplifier. The measuring resistor 11 is arranged between the amplifier 10 and the input 5 of the transmitting coil 3. The capacitor 12 is electrically connected in parallel to the transmitting coil 3. To set an operating point, the control unit 7 also has the DC signal source 13 and the amplifier 14. The DC signal source 13 generates a constant DC voltage of 1.5V and the second amplifier 14 has a gain of 1 and thus also serves as a buffer amplifier. The first amplifier 10 and the second amplifier 14 are fed with a DC voltage of 3V by the supply source 15. The terminating resistor 16 with the resistance $R_A$ is electrically connected in parallel with the receiving coil 4. The electrical resistance of the medium 8 between the transmitting coil 3 and the receiving coil 4 is $R_W$. The conductivity of the medium 8 is generally determined from the electrical resistance value $R_W$ of the medium 8 and the geometry of the medium 8 between the transmitting coil 3 and the receiving coil 4.

The transmitting coil 3 and the receiving coil 4 are inductively coupled by the electrically conductive medium 8—as already mentioned. The inductive coupling takes place in that the transmit alternating signal $U_S$ fed into the transmission coil 3 generates eddy currents in the medium 8, and the eddy currents in the receiving coil 4 induce the receive alternating signal $U_E$. Thus, the preset alternating signal $U_V$ causes the receive alternating signal $U_E$ via the transmit alternating signal $U_S$.

The control unit 7 is designed to vary the angular frequency $\omega$ of the preset alternating signal $U_V$ in a frequency interval, to determine, in the frequency interval, a frequency-dependent minimum input impedance at the input 5 of the transmitting coil 3 using the response alternating signal $U_M$ across the measuring resistor 11, to determine a minimum frequency of the response alternating signal $U_M$ at the minimum input impedance at the input 5 of the transmitting coil 3 and to determine a conductivity of the medium 8 using the minimum frequency of the response alternating signal $U_M$. In this case, the alternating signal source 9 generates the preset alternating signal $U_V$, the first amplifier 10 amplifies the preset alternating signal $U_V$ by a factor of 1 and the preset alternating signal $U_V$ causes the response alternating signal $U_M$ across the measuring resistor 11 in the form of a voltage, on the one hand, and on the other hand, the transmit alternating signal $U_S$ in the form of a voltage.

In this embodiment of the inductive conductivity measuring device 1, the transmitting coil 3, the receiving coil 4, the medium 8 and the capacitor 12 form a resonant circuit with a resonant frequency. The resonant circuit is a function which, taken in isolation, has no spatial configuration. In this case, both the transmitting coil 3 and the receiving coil 4 have, in addition to inductive components, parasitic capacitive components that affect the resonant circuit. Since the resonant frequency corresponds to the minimum frequency, the minimum input impedance at the input of the transmitting coil 3 is given at resonance of the resonant circuit, i.e., at resonant frequency, wherein the minimum input impedance is accompanied by a maximum amplitude of the response alternating signal $U_M$. The amplitude of the response alternating signal $U_M$ over the frequency interval is determined, for example, with an analog lock-in amplifier and then the maximum amplitude in the course of the amplitude over the frequency interval.

Figure 3:
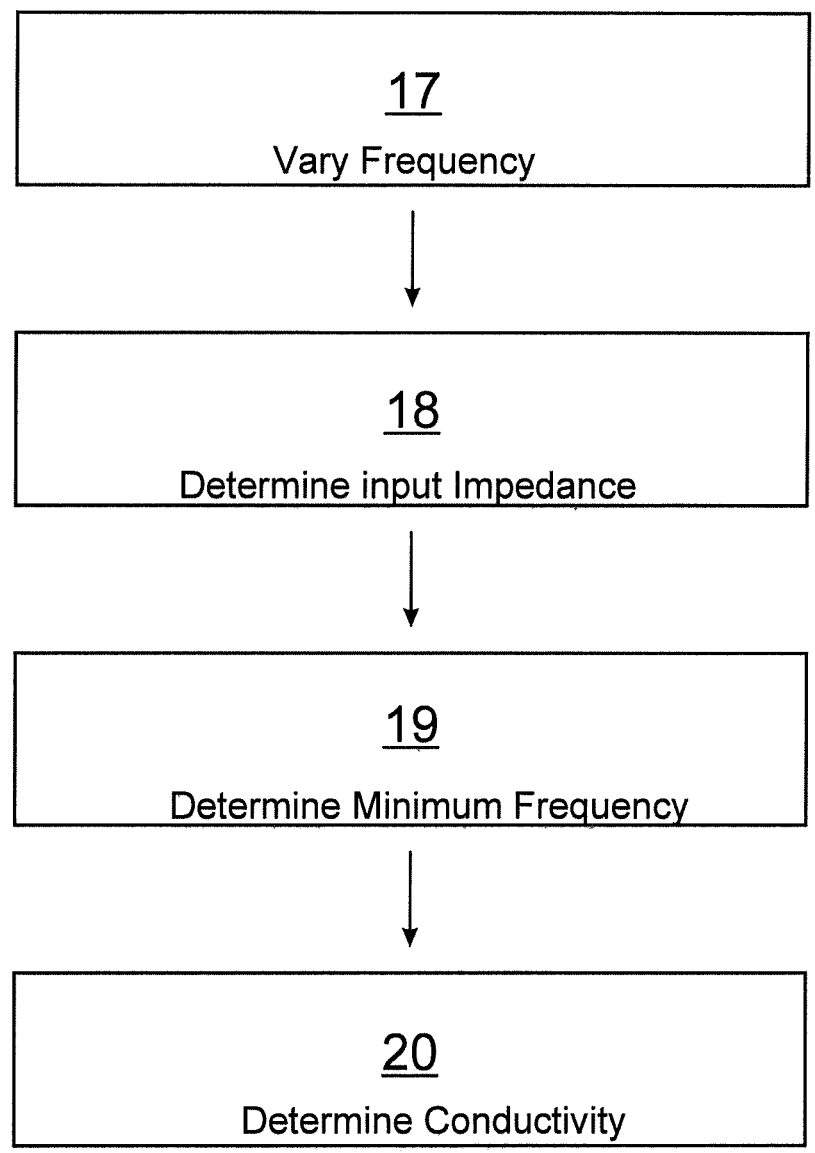
FIG. 3 is a flow chart of an embodiment of a method for operating the inductive conductivity measuring device of FIG. 1.

Since the inductive conductivity measuring device 1 is in operation, the control unit 7 carries out the method shown in the flow chart in FIG. 3 with the following process steps.

In a first method step 17, the electrical preset alternating signal $U_V$ is generated by the alternating signal source 9 and fed to the input 5 of the transmitting coil 3 and the angular frequency $\omega$ of the preset alternating signal $U_V$ is varied in a frequency interval.

In a second method step 18, a frequency-dependent minimum input impedance at the input 5 of the transmitting coil 3 is determined in the frequency interval using the response alternating signal $U_M$.

In a third method step 19, a minimum frequency of the response alternating signal $U_M$ is determined at the minimum input impedance at the input 5 of the transmitting coil 3.

In a fourth method step 20, a conductivity of the medium 8 is determined using the minimum frequency of the response alternating signal $U_M$.

What is claimed is:

1. A method for operating an inductive conductivity measuring device that has a transmitting coil with an input and a receiving coil inductively coupled to the transmitting coil by an electrically conductive medium, comprising the steps of:
   generating an electrical preset alternating signal and feeding the signal to the input of the transmitting coil,
   varying a frequency of the preset alternating signal in a frequency interval,
   in the frequency interval, determining a frequency-dependent minimum input impedance at the input of the transmitting coil using a response alternating signal,
   determining a minimum frequency of the response alternating signal at the minimum input impedance of the input of the transmitting coil, and
   determining a conductivity of the medium using the minimum frequency of the response alternating signal.

2. The method according to claim 1, wherein the transmitting coil, the receiving coil and the medium form an electrical resonant circuit having a resonant frequency, wherein, in determining the minimum input impedance and the minimum frequency, the resonant frequency of the resonant circuit is determined.

3. The method according to claim 1, wherein the conductivity measuring device has a measuring resistor at the input of the transmitting coil, wherein a measuring voltage is measured across the measuring resistor as the response alternating signal.

4. An inductive conductivity measuring device, comprising:
   a transmitting coil having an input,
   a receiving coil and
   a control unit,
   wherein the control unit is adapted to generate an electrical preset alternating signal and to supply the preset alternating signal to the input of the transmitting coil, and
   wherein, during operation, the transmitting coil and the receiving coil are inductively coupled to one another by an electrically conductive medium,
   wherein the control unit, during operation, is adapted to vary a frequency of the preset alternating signal in a frequency interval, to determine, in the frequency interval, a frequency-dependent minimum input impedance at the input of the transmitting coil using a response alternating signal ($U_M$), to determine a minimum frequency of the response alternating signal at the minimum input impedance at the input of the transmitting coil, and to determine a conductivity of the medium using the minimum frequency of the response alternating signal.

5. The inductive measuring device according to claim 4, wherein the receiving coil has an input and the input is terminated with a terminating resistor.

* * * * *